United States Patent
Kang et al.

(10) Patent No.: US 8,921,767 B2
(45) Date of Patent: Dec. 30, 2014

(54) AUTOMATIC CALIBRATION OF FOURIER-DOMAIN OPTICAL COHERENCE TOMOGRAPHY SYSTEMS

(75) Inventors: Jin Kang, Ellicott City, MD (US); Marcin Arkadiusz Balicki, Baltimore, MD (US); Xuan Liu, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 95 days.

(21) Appl. No.: 13/813,611

(22) PCT Filed: Aug. 2, 2011

(86) PCT No.: PCT/US2011/046290
§ 371 (c)(1), (2), (4) Date: Jan. 31, 2013

(87) PCT Pub. No.: WO2012/018832
PCT Pub. Date: Feb. 9, 2012

(65) Prior Publication Data
US 2013/0128267 A1   May 23, 2013

Related U.S. Application Data

(60) Provisional application No. 61/370,020, filed on Aug. 2, 2010.

(51) Int. Cl.
*G01D 18/00* (2006.01)
*G12B 13/00* (2006.01)
*G01B 9/02* (2006.01)
*G01N 21/47* (2006.01)

(52) U.S. Cl.
CPC ........ *G01B 9/02091* (2013.01); *G01B 9/02044* (2013.01); *G01N 21/4795* (2013.01); *G01B 9/02074* (2013.01)
USPC ...................................... 250/252.1

(58) Field of Classification Search
CPC ................. G01B 9/02091; G01B 9/02044
USPC ...................................... 250/252.1
See application file for complete search history.

(56) References Cited

U.S. PATENT DOCUMENTS 5,631,469 A * 5/1997 Carrieri et al. ............. 250/341.5
5,705,787 A * 1/1998 Karanassios ............. 219/121.52

(Continued)

OTHER PUBLICATIONS

Ahmad et al., "Cross-correlation-based image acquisition technique for manually-scanned optical coherence tomography," Opt. Express 17, 8125-8136 (2009).

(Continued)

*Primary Examiner* — David Porta
*Assistant Examiner* — Abra Fein
(74) *Attorney, Agent, or Firm* — Venable LLP; Henry J. Daley

(57) ABSTRACT

A method for calibrating a Fourier domain optical coherence tomography system includes receiving spectral data from an optical detector comprising a linear array of detector elements, each detector element having a position labeled n, wherein detected light was wavelength-dispersed across the linear array of detector elements; determining parameters of a preselected functional relationship between wave number, kn, corresponding to detector element n as a function of optical detector element n based on the spectral data; further receiving subsequent spectral data subsequent to the first-mentioned receiving, wherein detected light was wavelength-dispersed across the linear array of detector elements; converting the subsequent spectral data using the preselected functional relationship between wave number kn and optical detector element n to obtain converted spectral data; and performing an inverse Fourier transform of the converted spectral data to obtain a depth profile.

27 Claims, 11 Drawing Sheets

(56) References Cited

U.S. PATENT DOCUMENTS

| | | | |
|---|---|---|---|
| 7,480,058 | B2 | 1/2009 | Zhao et al. |
| 2004/0046109 | A1* | 3/2004 | Chen et al. ............... 250/227.14 |
| 2006/0195271 | A1* | 8/2006 | Park .............................. 702/27 |
| 2008/0181477 | A1 | 7/2008 | Izatt et al. |
| 2009/0015842 | A1 | 1/2009 | Leitgeb et al. |
| 2010/0174494 | A1* | 7/2010 | De Peinder et al. ............ 702/30 |
| 2010/0200104 | A1* | 8/2010 | Fleischer et al. .................. 141/1 |

OTHER PUBLICATIONS

Azimi et al., "Real-time and high-performance calibration method for high-speed swept-source optical coherence tomography," J Biomed Opt., 15(1):016005 (2010).

Balicki et al., "Single Fiber Optical Coherence Tomography Microsurgical Instruments for Computer and Robot-Assisted Retinal Surgery", Proceedings of the MICCAI Conference, London, pp. 108-115 (2009).

Chen et al., "Densely folded spectral images of a CCD spectrometer working in the full 200-1000nm wavelength range with high resolution", Opt. Express 13, 1004910054 (2005).

Choma et al., "Sensitivity advantage of swept source and Fourier domain optical coherence tomography," Opt. Express 11, 2183-2189 (2003).

de Boer et al., "Improved signal-to-noise ratio in spectral-domain compared with time-domain optical coherence tomography," Opt. Lett. 28, 2067-2069 (2003).

Ding et al., "A new spectral calibration method for Fourier domain optical coherence tomography", Opt. Int. J. Light Electron. Opt. (2009).

Fercher et al., "Optical coherence tomography—principles and applications," Rep. Prog. Phys. 66, 239-303 (2003).

Han et al., "Common-path Fourier-domain Optical Coherence Tomography with a Fiber Optic Probe Integrated Into a Surgical Needle"; Proceedings of CLEO Conference (2009).

Han et al., "Handheld forward-imaging needle endoscope for ophthalmic optical coherence tomography inspection", Journal of Biomedical Optics 13, 020505 (2008).

Iftimia et al., "Dual-beam Fourier domain optical Doppler tomography of zebrafish," Opt. Express 16, 13624-13636 (2008).

Kang et al., "Endoscopic Functional Fourier Domain Common Path Optical Coherence Tomography for Microsurgery," IEEE J. of Select. Topic in Quantum. Electron. 10.1109/JSTQE.2009.2031597, (2010).

Leitgeb et al., "Performance of Fourier domain vs. time domain optical coherence tomography," Appl. Opt. Express 11, 889-894 (2003).

Li et al., "Signal-to-noise ratio analysis of all-fiber common-path optical coherence tomography," Appl. Opt. 47, 4833-4840 (2008).

Liu et al., "Fiber-optic Fourier-domain common-path OCT," Chin. Opt. Lett. 6, 899-901 (2008).

Liu et al., "Internal limiting membrane layer visualization and vitreoretinal surgery guidance using OCT integrated microsurgical tool," Proceedings of SPIE vol. 7550, 755003 (2010).

Mujat et al., "Autocalibration of spectral-domain optical coherence tomography spectrometers for in vivo quantitative retinal nerve fiber layer birefringence determination", J Biomed Opt., 12(4):041205 (2007).

Sharma et al., "All-fiber Fizeau optical coherence tomography: sensitivity optimization and system analysis," IEEE J. Quantum Electron. 11799-805(2005).

Tao et al., "Intraoperative spectral domain optical coherence tomography for vitreoretinal surgery," Opt. Lett. 35, 3315-3317 (2010).

Uneri et al., "New Steady-Hand Eye Robot with Microforce Sensing for Vitreoretinal Surgery Research", IEEE BioRob (2010).

Wojtkowski et al., "Ultrahigh-resolution, high-speed, Fourier domain optical coherence tomography and methods for dispersion compensation," Opt. Express 12, 2404-2422 (2004).

Xi et al., "Generic real-time uniform K-space sampling method for high-speed swept-Source optical coherence tomography," Opt. Express 18, 9511-9517 (2010).

Xu et al., "A zero-crossing detection method applied to Doppler OCT," Opt. Express 16, 4394-4412 (2008).

Yasuno et al., "In vivo high-contrast imaging of deep posterior eye by 1-urn swept source optical coherence tomography and scattering optical coherence angiography," Opt. Express 15, 6121-6139 (2007).

* cited by examiner

AUTOMATIC CALIBRATION OF FOURIER-DOMAIN OPTICAL COHERENCE TOMOGRAPHY SYSTEMS

CROSS-REFERENCE OF RELATED APPLICATION

This application claims priority to U.S. Provisional Application No. 61/370,020 filed Aug. 2, 2010, the entire contents of which are hereby incorporated by reference, and is a U.S. national stage application under 35 U.S.C. §371 of PCT/US2011/046290 filed Aug. 2, 2011, the entire contents of which are incorporated herein by reference.

This invention was made with Government support of Grant No. 1R01 EB 007969-01, awarded by the Department of Health and Human Services, The National Institutes of Health (NIH); and Grant No. EEC-9731478, awarded by the National Science Foundation (NSF). The U.S. Government has certain rights in this invention.

BACKGROUND

1. Field of Invention

The field of the currently claimed embodiments of this invention relates to Fourier domain optical coherence tomography systems (FD-OCT) and more particularly to methods of automatically calibrating FD-OCT systems.

2. Discussion of Related Art

Integrating optical coherence tomography (OCT) in handheld or robot-assisted surgical tools for microsurgery can potentially minimize damage to tissue and improve surgical outcomes. See the following for some examples of applications where methods according to some embodiments of the current invention can be utilized:

- S. Han, M. V. Sarunic, J. Wu, M. Humayun, and C. Yang, "Handheld forward-imaging needle endoscope for ophthalmic optical coherence tomography inspection", Journal of Biomedical Optics 13, 020505 (2008);
- M. Balicki, J. Han, I. Iordachita, P. Gehlbach, J. Handa, J. U. Kang, R. Taylor, "Single Fiber Optical Coherence Tomography Microsurgical Instruments for Computer and Robot-Assisted Retinal Surgery", Proceedings of the MICCAI Conference, London, pp. 108-115 (2009);
- K. Zhang, W. Wang, J. Han and J. U. Kang, "A surface topology and motion compensation system for microsurgery guidance and intervention based on common-path optical coherence tomography," IEEE Transactions on Biomedical Engineering, Vol. 56, pp. 2318-2311 (2009);
- J. Han, M. Balicki, K. Zhang, X. Liu, J. Handa, R. Taylor, and J. U. Kang, "Common-path Fourier-domain Optical Coherence Tomography with a Fiber Optic Probe Integrated Into a Surgical Needle"; Proceedings of CLEO Conference (2009); and
- Y. K. Tao, J. P. Ehlers, C. A. Toth, and J. A. Izatt, "Intraoperative spectral domain optical coherence tomography for vitreoretinal surgery," Opt. Lett. 35, 3315-3317 (2010).

Fourier Domain OCT (FD OCT), which offers significantly improved sensitivity and imaging speed compared to time-domain OCT (TD-OCT) (J. de Boer, B. Cense, B. Hyle Park, M. C. Pierce, G. J. Tearney, and B. E. Bouma, "Improved signal-to-noise ratio in spectral-domain compared with time-domain optical coherence tomography," Opt. Lett. 28, 2067-2069 (2003); R. Leitgeb, C. Hitzenberger, and Adolf Fercher, "Performance of Fourier domain vs. time domain optical coherence tomography," Opt. Express 11, 889-894 (2003); M. Choma, M. Sarunic, C. Yang, and J. Izatt, "Sensitivity advantage of swept source and Fourier domain optical coherence tomography," Opt. Express 11, 2183-2189 (2003); X. Li, J. Han, X. Liu, and J. U. Kang, "Signal-to-noise ratio analysis of all-fiber common-path optical coherence tomography," Appl. Opt. 47, 4833-4840 (2008); U. Sharma, N. M. Fried, and J. U. Kang, "All-fiber Fizeau optical coherence tomography: sensitivity optimization and system analysis," IEEE J. Quantum Electron. 11799-805 (2005); X. Liu, X. Li, D. Kim, I. Ilev, and J. U. Kang, "Fiber-optic Fourier-domain common-path OCT," Chin. Opt. Lett. 6, 899-901 (2008)), has been incorporated with robotic surgical tools for vitreoretinal surgery applications. For example, such systems can use real-time, tool-to-tissue range data derived from OCT images to actively enforce safety barriers, compensate for patient motion, or guide the surgeon to perform a pre-planned maneuver (M. Balicki, J. Han, I. Iordachita, P. Gehlbach, J. Handa, J. U. Kang, R. Taylor, "Single Fiber Optical Coherence Tomography Microsurgical Instruments for Computer and Robot-Assisted Retinal Surgery", Proceedings of the MICCAI Conference, London, pp. 108-115 (2009); K. Zhang, W. Wang, J. Han and J. U. Kang, "A surface topology and motion compensation system for microsurgery guidance and intervention based on common-path optical coherence tomography," IEEE Transactions on Biomedical Engineering, Vol. 56, pp. 2318-2311 (2009)). In such applications, it is critical for OCT to have high axial imaging resolution and precise depth ranging functionality. Further, safety, reliability, and ease of use are important factors in a demanding application like microsurgery, where imaging devices are exposed to extreme handling conditions, require frequent safety checks, and redundant monitoring during operation.

FD OCT has two subcategories: 1) spectral domain OCT and 2) swept-source OCT (A. F. Fercher, W. Drexler, C. K. Hitzenberger and T. Lasser, "Optical coherence tomography—principles and applications," Rep. Prog. Phys. 66, 239-303 (2003); B. E. Bouma and G. J. Tearney, "Handbook of Optical Coherence Tomography", Marcel Dekker, New York (2002)). In this specification, "FD OCT" specifically refers to spectral domain OCT, which uses a spectrometer to detect spectral interferograms. This is typically an inexpensive approach. To achieve high axial resolution and ranging accuracy, FD OCT requires not only a broadband light source and a well-designed spectrometer, but also an accurate spectral calibration to correctly reconstruct the sample's depth profile (A-scan). To obtain an A-scan from the spectral interferogram captured by the spectrometer, an inverse Fourier transformation is applied to the interference spectral data that is evenly spaced in wavenumber space (k-space). See, for example:

- Y. Chen, B. Sun, T. Han, Y. Kong, C. Xu, P. Zhou, X. Li, S. Wang, Y. Zheng, L. Chen, "Densely folded spectral images of a CCD spectrometer working in the full 200-1000 nm wavelength range with high resolution", Opt. Express 13, 10049-10054 (2005);
- M. Mujat, B. H. Park, B. Cense, T. C. Chen, J. de Boer, "Autocalibration of spectral-domain optical coherence tomography spectrometers for in vivo quantitative retinal nerve fiber layer birefringence determination", J Biomed Opt., 12(4):041205 (2007);
- C. Ding, P. Bu, X. Wang, O. Sasakic, "A new spectral calibration method for Fourier domain optical coherence tomography", Opt. Int. J. Light Electron. Opt. (2009);
- E. Azimi, B. Liu, M. E. Brezinski., "Real-time and high-performance calibration method for high-speed swept-source optical coherence tomography," J Biomed Opt., 15(1):016005 (2010);

J. Xi, L. Huo, J. Li, and X. Li, "Generic real-time uniform K-space sampling method for high-speed swept-Source optical coherence tomography," Opt. Express 18, 9511-9517 (2010)

However, in FD OCT, the spectra are detected by CCD or CMOS arrays, which usually do not guarantee a uniform sampling in k-space. Converting the data from pixel space to k-space depends on knowing the wavenumber at each pixel of the array detector, which is usually determined through a calibration process. Poor or imprecise calibration results in a point spread function (PSF) that has a depth-dependent broadening, analogous to pulse broadening induced by group velocity dispersion. Besides significantly degrading system performance in terms of the resolution and sensitivity, an inaccurate calibration also leads to erroneous depth ranging.

Calibration of a spectrometer in FD OCT can be achieved either by measuring the spectrum of an external calibrating light source with known spectral features (Y. Chen, B. Sun, T. Han, Y. Kong, C. Xu, P. Zhou, X. Li, S. Wang, Y. Zheng, L. Chen, "Densely folded spectral images of a CCD spectrometer working in the full 200-1000 nm wavelength range with high resolution", Opt. Express 13, 10049-10054 (2005)) or by comparing spectral interferograms measured with the OCT spectrometer to measurements made by a well-calibrated commercial optical spectrum analyzer (OSA) (C. Ding, P. Bu, X. Wang, O. Sasakic, "A new spectral calibration method for Fourier domain optical coherence tomography", Opt. Int. J. Light Electron. Opt. (2009)). However, these conventional calibration methods are time-consuming and require separate measurements and extra equipment. These factors make conventional calibrations inconvenient in a clinical setting. Moreover, the characteristics of a spectrometer will naturally change over time, due both to environmental effects such as temperature and vibration and to poor handling practices (M. Mujat, et al). Therefore, monitoring and recalibration of the spectrometer may be necessary for each FD OCT measurement session. Furthermore, when using OCT in imaging and servoing for image-guided, robot-assisted surgery, the refractive index of the medium might be unknown and thus will impose a challenge in accurately determining the distance between the probe and sample surfaces. Since OCT measures optical path length, which is the product of physical distance and the medium's refractive index, a wrong estimation of this physical distance can cause inaccuracies in imaging, targeting errors, and robot control instabilities. All are unacceptable for high-risk microsurgical applications. A simple and automatic OCT calibration protocol that addresses these issues is required.

M. Mujat et al reported an automatic spectrometer calibration, based on generating a perfect sinusoidal spectral modulation in k-space by inserting a thin glass slide into the optical path ((M. Mujat, et al). The algorithm used requires that the spectrum has a perfect sinusoidal modulation; otherwise, it is impossible to obtain the phase for calibration. Moreover, M. Mujat et al's calibration does not produce the values for wavenumber limits; therefore, the physical pixel spacing of the OCT A-scan is still unclear after calibration. The specular reflection of the inserted glass slide may occupy a large portion of the detector's dynamic range, thus may reduce the dynamic range usable for sample and reference signal; on the other hand, the reduction of power from the broadband source may reduce the system's sensitivity. In Iftimia et al's spectral calibration, they circumvented the abovementioned problems by inserting the glass slide into the reference arm with power attenuation (N. V. Iftimia, D. X. Hammer, R. D. Ferguson, M. Mujat, D. Vu, and A. A. Ferrante, "Dual-beam Fourier domain optical Doppler tomography of zebrafish," Opt. Express 16, 13624-13636 (2008)). Therefore, there remains a need for improved methods and systems for calibrating FD OCT systems.

SUMMARY

A method for calibrating a Fourier domain optical coherence tomography system according to an embodiment of the current invention includes receiving spectral data from an optical detector comprising a linear array of detector elements, each detector element having a position labeled n, wherein detected light was wavelength-dispersed across the linear array of detector elements; determining parameters of a preselected functional relationship between wave number, $k_n$, corresponding to detector element n as a function of optical detector element n based on the spectral data; further receiving subsequent spectral data subsequent to the first-mentioned receiving, wherein detected light was wavelength-dispersed across the linear array of detector elements; converting the subsequent spectral data using the preselected functional relationship between wave number $k_n$ and optical detector element n to obtain converted spectral data; and performing an inverse Fourier transform of the converted spectral data to obtain a depth profile.

A computer readable medium according to an embodiment of the current invention includes software, which software when executed by a computer causes the computer to receive spectral data from an optical detector comprising a linear array of detector elements, each detector element having a position labeled n, wherein detected light was wavelength-dispersed across the linear array of detector elements; determine parameters of a preselected functional relationship between wave number, $k_n$, corresponding to detector element n as a function of optical detector element n based on the spectral data; further receive subsequent spectral data subsequent to the first-mentioned receiving, wherein detected light was wavelength-dispersed across the linear array of detector elements; convert the subsequent spectral data using the preselected functional relationship between wave number $k_n$ and optical detector element n to obtain converted spectral data; and perform an inverse Fourier transform of the converted spectral data to obtain a depth profile.

An automatic spectral calibration optical coherence system according to an embodiment of the current invention includes a reference, an optical probe, a light source optically coupled to the optical probe, a spectrometer detection system optically coupled to the optical probe, and a computer constructed to communicate with the spectrometer detection system while in operation. The computer is configured to receive spectral data from an optical detector comprising a linear array of detector elements, each detector element having a position labeled n, wherein detected light was wavelength-dispersed across the linear array of detector elements; determine parameters of a preselected functional relationship between wave number, $k_n$, corresponding to detector element n as a function of optical detector element n based on the spectral data; further receive subsequent spectral data subsequent to the first-mentioned receiving, wherein detected light was wavelength-dispersed across the linear array of detector elements; convert the subsequent spectral data using the preselected functional relationship between wave number $k_n$ and optical detector element n to obtain converted spectral data; and perform an inverse Fourier transform of the converted spectral data to obtain a depth profile.

BRIEF DESCRIPTION OF THE DRAWINGS

Further objectives and advantages will become apparent from a consideration of the description, drawings, and examples.

DETAILED DESCRIPTION

Figure 1A:
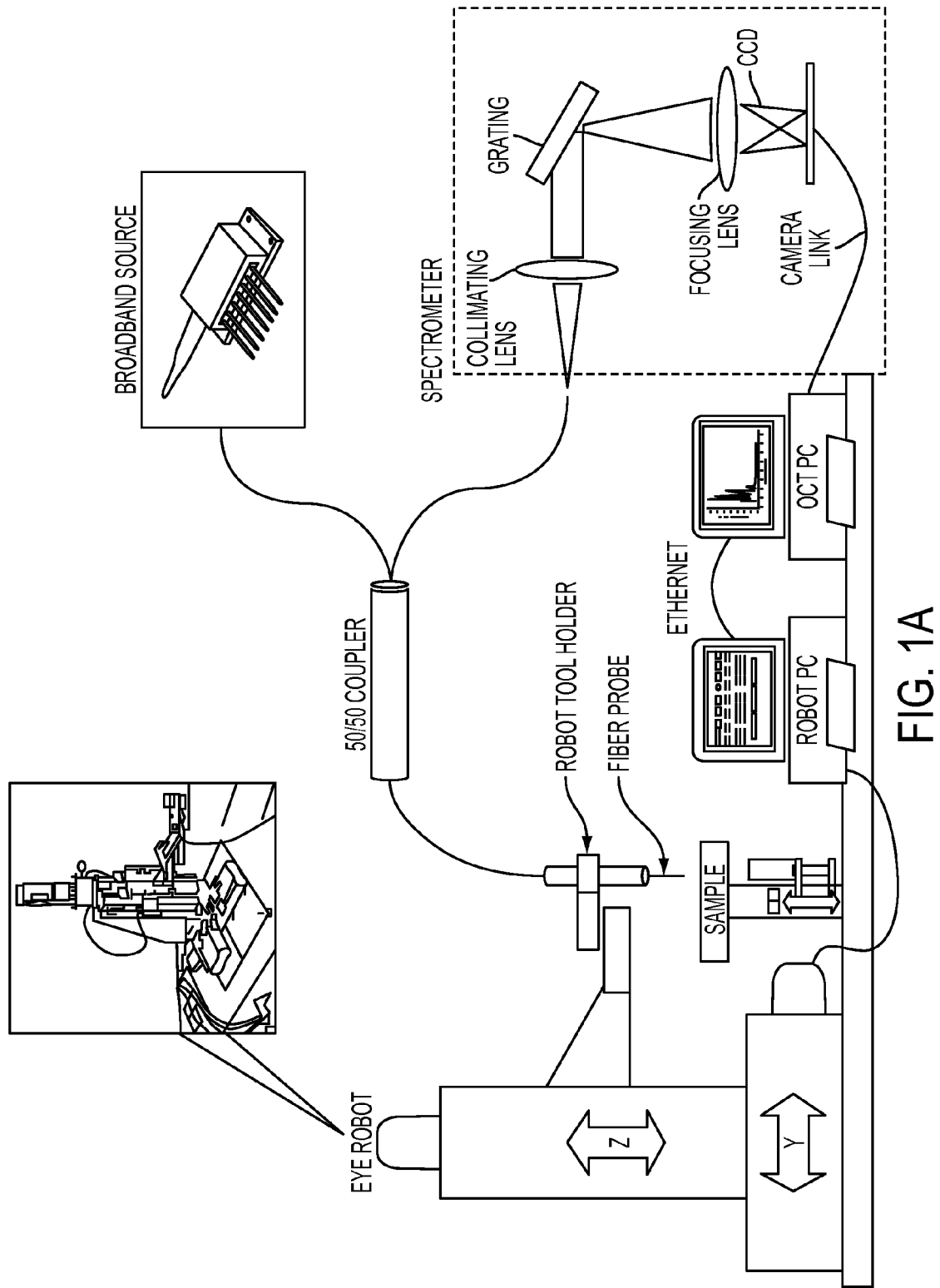
FIG. 1A provides a schematic illustration of an automatic spectral calibration optical coherence system according to an embodiment of the current invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

According to some embodiments of the current invention, we present a new automatic spectral calibration method for FD OCT. The method was tested using a common path FD OCT integrated with a robotic microsurgical assistant system called the EyeRobot (M. Balicki, J. Han, I. Iordachita, P. Gehlbach, J. Handa, J. U. Kang, R. Taylor, "Single Fiber Optical Coherence Tomography Microsurgical Instruments for Computer and Robot-Assisted Retinal Surgery", Proceedings of the MICCAI Conference, London, pp. 108-115 (2009); A. Uneri, M. Balicki, J. Handa, P. Gehlbach, R. Taylor, I. Iordachita "New Steady-Hand Eye Robot with Microforce Sensing for Vitreoretinal Surgery Research", IEEE BioRob (2010)). However, our calibration is essentially a generic, automatic spectral calibration (ASC) method that can be implemented in any spectrometer-based FD OCT system coupled with a precise axial positioning actuator, which is often used in OCT scanners.

The ASC method according to some embodiments of the current invention does not require the use of an external light source or a commercial OSA. Moreover, we use a zero-crossing detection technique according to some embodiments of the current invention which offers an accurate estimation of the functional dependence of wavenumber on pixel index. Zero-crossing detection enables us to extract such dependency with high accuracy even when the spectrum does not have a perfect sinusoidal modulation. According to some embodiments of the current invention, we further correct the spectral mapping obtained from zero-crossing detection using an iterative optimization (M. j Wojtkowski, V. Srinivasan, T. Ko, J. Fujimoto, A. Kowalczyk, and J. Duker, "Ultrahigh-resolution, high-speed, Fourier domain optical coherence tomography and methods for dispersion compensation," Opt. Express 12, 2404-2422 (2004); Y. Yasuno, Y. Hong, S. Makita, M. Yamanari, M. Akiba, M. Miura, and T. Yatagai, "In vivo high-contrast imaging of deep posterior eye by 1-um swept source optical coherence tomography and scattering optical coherence angiography," Opt. Express 15, 6121-6139 (2007)). As a result, spectral interferograms used in our ASC method can be directly derived from an arbitrary sample—even with complex internal structures like the ones found in biological samples. Therefore, a specimen itself can be used to generate data to calibrate the OCT system during scanning. To extract the pixel spacing of an OCT A-scan according to an embodiment of the current invention, we adjust the axial distance between the reference plane and the sample surface by the commanded motion of a robot which holds the probe of an FD OCT. The pixel spacing is obtained through a least square linear regression based on the known robot motion and the depth ranging derived from the OCT signal. Furthermore, in the case where the sample could be moving, we modulate the motion of the robot sinusoidally to encode its position relative to the moving sample. The motion is then extracted from the A-scans to calculate the physical pixel spacing.

FIG. 1A provides a schematic illustration of an automatic spectral calibration optical coherence system according to an embodiment of the current invention. The automatic spectral calibration optical coherence system includes an optical fiber probe, a light source optically coupled to the optical fiber probe, a spectrometer detection system optically coupled to the optical fiber probe, and a computer constructed to communicate with the spectrometer detection system while in operation. The computer is configured to perform automatic spectral calibration according to methods of the current invention.

Figure 1B:
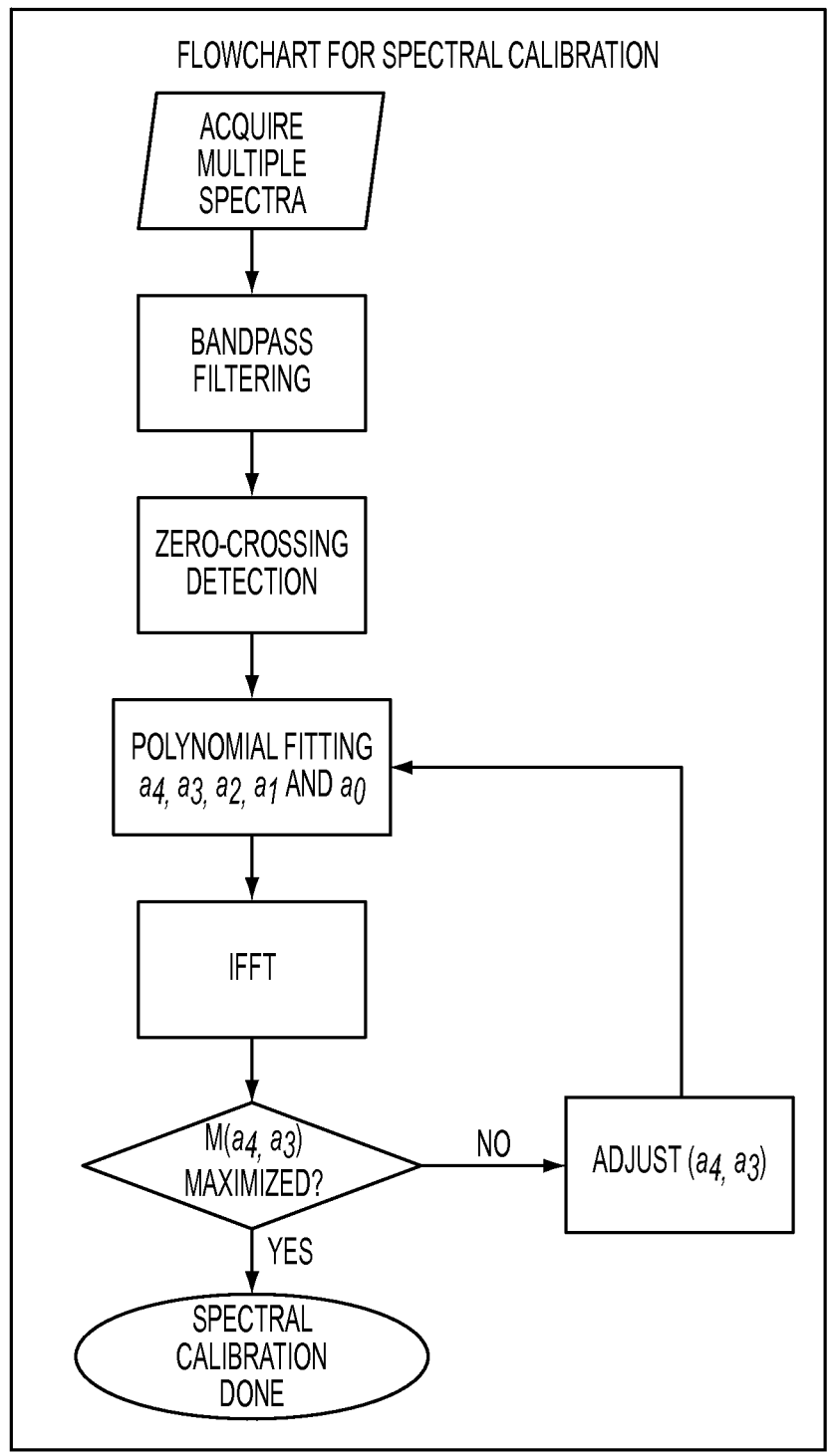
FIG. 1B provides a flow chart illustrating methods for calibrating a Fourier domain optical coherence tomography system according to some embodiments of the current invention.

FIG. 1B is a flow chart illustrating methods for calibrating a Fourier domain optical coherence tomography system according to some embodiments of the current invention. The method includes receiving spectral data from an optical detector comprising a linear array of detector elements, each detector element having a position labeled n, wherein detected light was wavelength-dispersed across the linear array of detector elements; determining parameters of a preselected functional relationship between wave number, $k_n$, corresponding to detector element n as a function of optical detector element n based on the spectral data; further receiving subsequent spectral data subsequent to the first-mentioned receiving, wherein detected light was wavelength-dispersed across the linear array of detector elements; converting the subsequent spectral data using the preselected functional relationship between wave number $k_n$ and optical detector element n to obtain converted spectral data; and performing an inverse Fourier transform of the converted spectral data to obtain a depth profile.

The preselected functional relationship can be a polynomial according to some embodiments of the current invention. The preselected functional relationship can be the following $$k_n = a_4 n^4 + a_3 n^3 + a_2 n^2 + a_1 n + a_0$$

wherein the determining parameters is determining parameters $a_0$, $a_1$, $a_2$, $a_3$, and $a_4$.

The method can further include determining parameters using a zero crossing analysis of the spectral data. The determining parameters can further include an iterative process taking into account a sharpness of an interferogram based on the spectral data.

The method according to some embodiments of the current invention can further include calibrating a depth corresponding to each detector element of the linear array of detector elements. The calibrating a depth can include moving a distal end of an optical probe of the Fourier domain optical coherence tomography system along a predefined path. The predefined path can be, but is not limited to, a substantially periodic path. For example, the predefined path can be a substantially sinusoidal path.

EXAMPLES

To test the performance of the calibration method according to an embodiment of the current invention, we measured the system's axial PSF at different imaging depths. The results showed an axial resolution better than 4 μm over the entire imaging depth of interest. After calibrating the A-scan pixel spacing, we achieved high ranging accuracy with a ranging error within the system's tolerance. We finally performed OCT scans to a multilayered phantom as well as to human subject in vivo in some further examples. Two-dimensional images revealing sample structure were obtained using automatic spectral calibration according to an embodiment of the current invention.

CP FD-OCT and Robotic Scanning System

According to an embodiment of the current invention, a Common Path FD-OCT (CP FD-OCT) is integrated with a robotic system, the EyeRobot in this example. CP FD OCT is a simple and compact system. It can provide a small probe size that facilitates integration of OCT with various robotic systems (M. Balicki, J. Han, I. Iordachita, P. Gehlbach, J. Handa, J. U. Kang, R. Taylor, "Single Fiber Optical Coherence Tomography Microsurgical Instruments for Computer and Robot-Assisted Retinal Surgery", Proceedings of the MICCAI Conference, London, pp. 108-115 (2009); X. Liu, E. Meisne; J. Han; K. Zhang, P. Gehlbach; R. Taylor; "Internal limiting membrane layer visualization and vitreoretinal surgery guidance using OCT integrated microsurgical tool," Proceedings of SPIE Vol. 7550, 755003 (2010)). The reference light in CP OCT is derived from the distal end of the probe, which is also the tool tip; therefore, the sample-reference distance measured by CP FD OCT is virtually the tool-to-tissue distance, which can be of great importance in robotic surgical servoing. Moreover, the shared reference and sample arms enable us to use a single-mode fiber probe with arbitrary length without concerns of chromatic dispersion mismatch (X. Li, J. Han, X. Liu, and J. U. Kang, "Signal-to-noise ratio analysis of all-fiber common-path optical coherence tomography," Appl. Opt. 47, 4833-4840 (2008); U. Sharma, N. M. Fried, and J. U. Kang, "All-fiber Fizeau optical coherence tomography: sensitivity optimization and system analysis," IEEE J. Quantum Electron. 11799-805 (2005); J. U. Kang, J. Han, X. Liu, K. Zhang, C. Song, and P. Gehlbach, "Endoscopic Functional Fourier Domain Common Path Optical Coherence Tomography for Microsurgery," IEEE J. of Select. Topic in Quantum. Electron. 10.1109/JSTQE.2009.2031597, (2010)).

As shown in FIG. 1A, the CP FD OCT system includes a single-mode fiber probe and a fiber-optic coupler which launches the source output to a sample as well as collects back reflected/scattered light. The tip of the single-mode fiber probe is cleaved at a right angle to provide the reference light. In this example, we use a broadband source in the CP FD OCT system to achieve high axial resolution. Three multiplexed superluminescent emission diodes (SLED) from Exolas Inc. have been found to be suitable for some applications to form a broadband source that has a central wavelength of 800 nm and full width half maximum of 106 nm. In one example, we built a custom spectrometer to detect the spectral interferograms for OCT image formation. This example has a collimator, 1200-line pair-per-mm diffraction grating, an achromatic lens with 100 mm focal length and a 2048 pixel CCD with 14 μm pixel size (e2v AVIIVA SM2 CL 2014, 28 kHz line scan rate). The camera integration time is set to 1 μs to avoid motion artifacts.

The robot in this example is a cooperatively controlled robotic assistant where the surgeon and robot both hold the surgical tool; the robot senses forces exerted by the surgeon on the tool handle and moves to comply with very high precision, inherently filtering out physiological hand tremor (A. Uneri, M. Balicki, J. Handa, P. Gehlbach, R. Taylor, I. Iordachita "New Steady-Hand Eye Robot with Microforce Sensing for Vitreoretinal Surgery Research", IEEE BioRob (2010)). Furthermore, the robot controller can quickly switch between and/or combine the following modes: user guidance; sensor-based guidance; or predefined autonomous motion profiles. In one example, we used only a Cartesian positioning subsystem of the EyeRobot that has three orthogonally mounted linear stages with positioning resolution of 1 μm and measured precision of about ±1 μm over the range of motion required for this example (<4 mm). The single-mode fiber probe of CP FD-OCT is attached to the tool holder of the EyeRobot, which scans the probe to obtain B-mode or C-mode OCT images, or actively servos surgical tasks (M. Balicki, J. Han, I. Iordachita, P. Gehlbach, J. Handa, J. U. Kang, R. Taylor, "Single Fiber Optical Coherence Tomography Microsurgical Instruments for Computer and Robot-Assisted Retinal Surgery", Proceedings of the MICCAI Conference, London, pp. 108-115 (2009)). The test samples are mounted on a separate actuated micrometer stage placed beneath the probe. The robot is guided directly by the operator to position the OCT probe above the desired scanning area of the sample.

The robot is interfaced to a PC workstation through a commercial motion controller (Galil DMC 1886), with software level servo loop operating at 500 Hz. A 6 degree of freedom (DOF) force-torque sensor (ATI Nano43) is mounted on the robot near the OCT probe as a user interface for cooperative, "hands-on" control. The OCT application is implemented on a separate PC and communicates with the robot PC via direct Ethernet link, with a fraction of ms latency.

The CP FD-OCT with a bare-fiber probe suffers from significant signal decay with increased imaging depth, especially above 500 μm. This is because without a focusing lens at the sample arm, the light beam exiting the fiber tip diverges significantly as it propagates farther. However, this is not an issue for our application where the tool for surgical intervention is placed extremely close to the interrogated tissue.

The following now describes methods of automatic calibration of CP FD-OCT systems according to some embodiments of the current invention. As a result of interference between the reference and sample light, a spectral interferogram can be obtained. $S_n$, the spectral intensity of the interference term detected by the $n^{th}$ pixel of the CCD, can be expressed as:

$$S_n = \alpha S_0(k_n) \sum_m [R_m \cos(2k_n l_m)] \quad (1)$$

In Equation (1), $k_n$ is the wavenumber corresponding to the $n^{th}$ element of the CCD array; $S_0$ indicates source spectrum; $l_m$ indicates the path length difference between reference and sample plane; $R_m$ indicates the sample reflectivity; and $\alpha$ is the system's responsivity.

When an inverse fast Fourier transformation (IFFT) is performed on the spectral interferogram to reconstruct the sample's depth profile, it requires that the spectral interferogram be evenly sampled in k-space. However, $k_n$ in Equation (1), usually does not depend linearly on n. Therefore $S_n$ has to be converted to k-space before IFFT (R. Leitgeb, et al; M. Choma, et al; A. F. Fercher, et al), which requires us to know the wavenumber corresponding to each pixel. According to an embodiment of the current invention, we assume that wavenumber $k_n$ has a $4^{th}$ order polynomial dependency on n, as follows:

$$k_n = a_4 n^4 + a_3 n^3 + a_2 n^2 + a_1 n + a_0. \quad (2)$$

A first task in ASC according to some embodiments of the current invention is to determine the coefficients (parameters) of the polynomial, i.e., $a_0$, $a_1$, $a_2$, $a_3$, and $a_4$.

M. Mujat et al. obtained the functional dependency of wavenumber on the pixel indices by retrieving the phase from spectral interferogram (M. Mujat, et al). However, when an arbitrary sample with complex internal structures is imaged, simply extracting the phase of interferogram, p(n), does not lead to a knowledge of $k_n$. Nevertheless, the spectral mapping may still be achieved according to some embodiments of the current invention by using a zero-crossing detection technique, which has been used in processing Doppler OCT signals (Z. Xu, L. Carrion, and R. Maciejko, "A zero-crossing detection method applied to Doppler OCT," Opt. Express 16, 4394-4412 (2008)). The zero-crossing detection for a spectrum is based on the fact that zero-crossing points in a spectral interferogram are almost evenly spaced in k-space with a spectral interval δk. Although signals come from different depths and result in different frequency components in the spectral interferogram, the surface reflection of the sample generates a large spectral modulation due to a refractive index discontinuity, and essentially determines the "fundamental frequency" of interference fringes, which is 1/δk.

To reduce the probability of error in zero-crossing detection according to some embodiments of the current invention, we first apply a bandpass filter centering at the fundamental frequency of the spectral interference fringes, which simultaneously removes the autocorrelation term or DC component in the spectrum. Afterwards, we calculate the zero-crossing points by finding all pairs of adjacent pixels that have signal values with opposite signs. The $m^{th}$ zero-crossing point $n_m$ is obtained using a simple linear triangulation formula as $$n_m = \frac{n_1 S_{n_1+1} - (n_1+1) S_{n_1}}{S_{n_1+1} - S_{n_1}} \quad (3)$$

in which $S_{n_1}$ and $S_{n_1+1}$ are spectral signal at the $n_1^{th}$ and $(n_1+1)^{th}$ pixels (Z. Xu, et al).

The wavenumbers corresponding to the zero-crossing points are known to be an integral multiple of δk plus a constant offset, as shown in Equation (4):

$$k(n_m) = m\delta k + k_0 \quad (4)$$

Translating and scaling $k(n_m)$, we have:

$$\tilde{k}(n_m) = \frac{k(n_m) - k_0}{\delta k} \quad (5)$$

Given that k(n) is a polynomial, and so is $\tilde{k}(n_m)$, the polynomial coefficients that define $\tilde{k}(n_m)$ can be found through least-squares polynomial fitting, using the known function value of $\tilde{k}(n_m)$ which is integer m, and the corresponding variable $n_m$. Therefore, with the polynomial obtained, the wavenumber at each pixel is known up to a scaling factor δk and an offset $k_0$. To convert the spectral data into wavenumber space, we generate an array $\hat{k}_n$, which has the same extremes as $\tilde{k}(n)$ and contains elements with evenly spaced values. Afterwards, we use a spline interpolation to obtain spectral data corresponding to wavenumbers in $\hat{k}_n$ using the detected signal corresponding to $\tilde{k}(n)$. Finally, performing IFFT on the spectral interferogram generated by interpolation will lead to an OCT A-scan.

Due to inevitable errors in zero-crossing detection, the polynomial coefficients obtained might be imprecise; therefore, the polynomial coefficients can be further refined according to some embodiments of the current invention. Since a more accurate spectral calibration allows us to reconstruct an OCT image with better energy concentration or image sharpness (J. U. Kang, J. Han, X. Liu, K. Zhang, C. Song, and P. Gehlbach, "Endoscopic Functional Fourier Domain Common Path Optical Coherence Tomography for Microsurgery," IEEE J. of Select. Topic in Quantum. Electron. 10.1109/JSTQE.2009.2031597, (2010); Z. Xu, et al), we may refine the polynomial coefficients by an iterative algorithm, which effectively maximizes the sharpness of OCT A-scans according to an embodiment of the current invention. A similar algorithm has been used in numerical dispersion compensation by correcting the nonlinear phase in ultrahigh resolution OCT. To measure the image sharpness, we use a quantity M (also defined in J. U. Kang, et al), which equals one divided by the total number of points in the A-scan with intensity larger than a predetermined threshold. Starting from an initial estimation of $a_4$, $a_3$, $a_2$, $a_1$ and $a_0$ based on the result of zero-crossing detection, we iteratively correct polynomial coefficients to maximize M through an unconstrained nonlinear optimization that searches the $(a_1, a_2, a_3, a_4)$ space. Although chromatic dispersion mismatch may also reduce energy concentration in the OCT image, image degradation induced by dispersion mismatch is negligible compared to the inaccuracy in calibration when CP FD-OCT is used, as in our case.

Zero-crossing detection is a critical step of ASC methods in some embodiments of the current invention, for it gives an accurate estimation of k(n), which provides the initial condition for the iterative correction to start with. The objective function of the optimization problem M may have multiple local optimums in the space searched. Starting from a point close to the global optimum, i.e., using a more accurate estimation of k(n), as the initial condition, the iteration can converge to the solution at a faster speed with higher reliability. Otherwise, it is likely that the iteration converges to a local optimum which does not correspond to the correct solution.

Figures 2A, 2B, 2C, 2D, 2E, 2F:
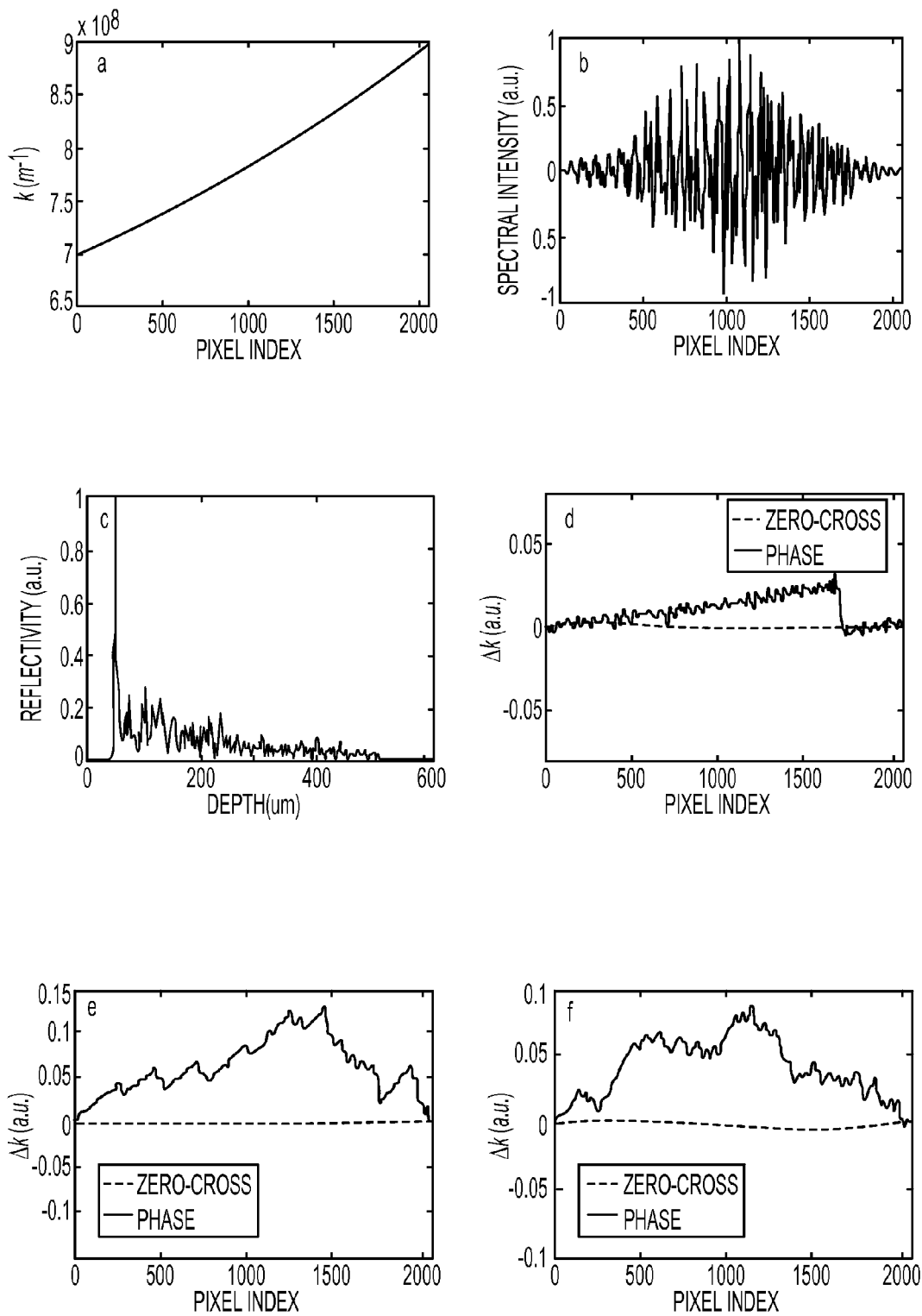
FIG. 2a shows wavenumber versus pixel index.
FIG. 2b simulated interferometric fringes in pixel space.
FIG. 2c A-scan corresponding to the spectrum in FIG. 2b; and differences between k(n) and k̃(n), k(n) and p(n) for data generated with R equals 0.1 FIG. 2d, 0.2 FIG. 2e, and 0.5 FIG. 2f for an example according to an embodiment of the current invention.

To show that that zero-crossing detection can offer a more accurate estimation of k(n) than from phase directly extracted from the real valued spectrum some embodiments of the current invention, we performed the following simulation. Assuming the spectrometer covers a spectral range from 700-900 nm and the CCD array samples the spectrum linearly in wavelength space, we calculated k(n) as shown in FIG. 2a, which would be used as a baseline to compare with the spectral mapping result we inversely extracted from our simulating data. FD-OCT signals were generated assuming that the sample has a unit reflectivity at 50 μm away from the reference, which is the sample surface; and we used uniformly distributed random numbers within [0 R] (R is a positive real value) to simulate the reflectivity from 50 μm to 500 μm in depth. Taking signal attenuation into consideration, we applied an exponential function with a decay constant of 200 μm to the depth profile. Modeling the source spectrum as a Gaussian function with a full width half maximum value of 90 nm, we generated an interferometric spectrum based on the simulated reflectivity profile according to Eq. (1). An example of the interferometric spectrum is shown in FIG. 2b (R=0.2), corresponding to the sample profile shown in FIG. 2c. Using the simulated spectral data, we can obtain k̃(n) by zero crossing detection; while we can also obtain the phase p(n) from the real valued spectrum by Hilbert transforming the spectrum shown in FIG. 2b. k(n), k̃(n) and p(n), are all resealed to [0, 1]. We show the difference between k(n) and k̃(n), k(n) and p(n) in FIGS. 2d-2f, in which R equals 0.1, 0.2, and 0.5, respectively. It is clear in FIGS. 2a-2f that zero-crossing detection offers a better estimation of k(n) than phase directly extracted from the interferometric spectrum.

Further embodiments of ASC methods according t the current invention can include obtaining the physical spacing between two adjacent pixels in OCT A-scan, Δz, which can be calculated using Equation (6) (M. Choma, et al.):

$$\Delta z = \frac{\pi}{\eta \Delta k} \quad (6)$$

Equation (6) can be used to calculate Δz using η, the medium's refractive index, and Δk, the spectral range covered by the spectrometer, both of which might be unknown in practice. As a result, instead of calculating Δz with Equation (6), we obtain Δz by comparing the commanded EyeRobot motion and ranging data derived from the OCT when we use the EyeRobot to precisely adjust the distance between the sample and reference plane.

With the single-mode fiber probe attached to the tool holder of the EyeRobot and a sample fixed to a stage, the distance between the reference plane and sample surface changes as the EyeRobot moves axially with respect to the sample surface. We recorded interferograms corresponding to different imaging depths. Converting spectral data to k-space based on obtained polynomial coefficients and performing IFFT, we obtain A-scans that have peaks indicating the interface between air and the surface of the sample. The indices of peak pixels are obtained by a peak searching algorithm and are denoted by $i_1$, $i_2$ and $i_3$ . . . , corresponding to different z-positions of the robot $Z_1$, $Z_2$ and $Z_3$ (K. Zhang, W. Wang, J. Han and J. U. Kang, "A surface topology and motion compensation system for microsurgery guidance and intervention based on common-path optical coherence tomography," IEEE Transactions on Biomedical Engineering, Vol. 56, pp. 2318-2311 (2009)). Using a vector i to indicate $i_1$, $i_2$ and $i_3$ . . . , a vector Z to indicate $Z_1$, $Z_2$ and $Z_3$ . . . , we have:

$$Z = i\Delta z + z_0 \quad (7)$$

The pixel spacing Δz can thus be obtained by regression using a least squares fit of the linear model shown above.

However, the ranging data derived from OCT, i.e., the pixel index of the A-scan peak, can be corrupted by the unknown motion of the sample. Such would be the case when trying to obtain calibration data from a live specimen. It therefore can be problematic to obtain the pixel spacing Δz based on Equation (7). However, a simple sinusoidal modulation of the EyeRobot Z position would allow us to easily differentiate the deterministic displacement of robot Z and random sample displacement $Z_S$. Although a sinusoidal modulation can be used in some embodiments, other deterministic motions, such as, but not limited to, other periodic motions can also be used according to other embodiments of the current invention. Taking into account the robot's known motion and the sample's random motion, we may rewrite Equation (7) as:

$$Z_0 \sin(\omega t) + Z_S(t) = i(t)\Delta z + z_0 \quad (8)$$

Due to the sinusoidal modulation of the EyeRobot Z position, performing Fourier transform on i(t) leads to a high peak corresponding to the modulation frequency ω. It is unlikely that the sample's motion has the same frequency component; therefore, filtering the signal corresponding to the modulation frequency out and denoting the result as î(t), which is related to the commanded motion of the probe, we have:

$$Z_0 \sin(\omega t) = \hat{i}\Delta z + \hat{z}_0 \quad (9)$$

Based on the linear model shown in Equation (9), we can obtain the pixel spacing Δz by least squares regression, even with unknown sample motion.

Experiments and Results

Figures 3A, 3B, 3C, 3D, 3E:
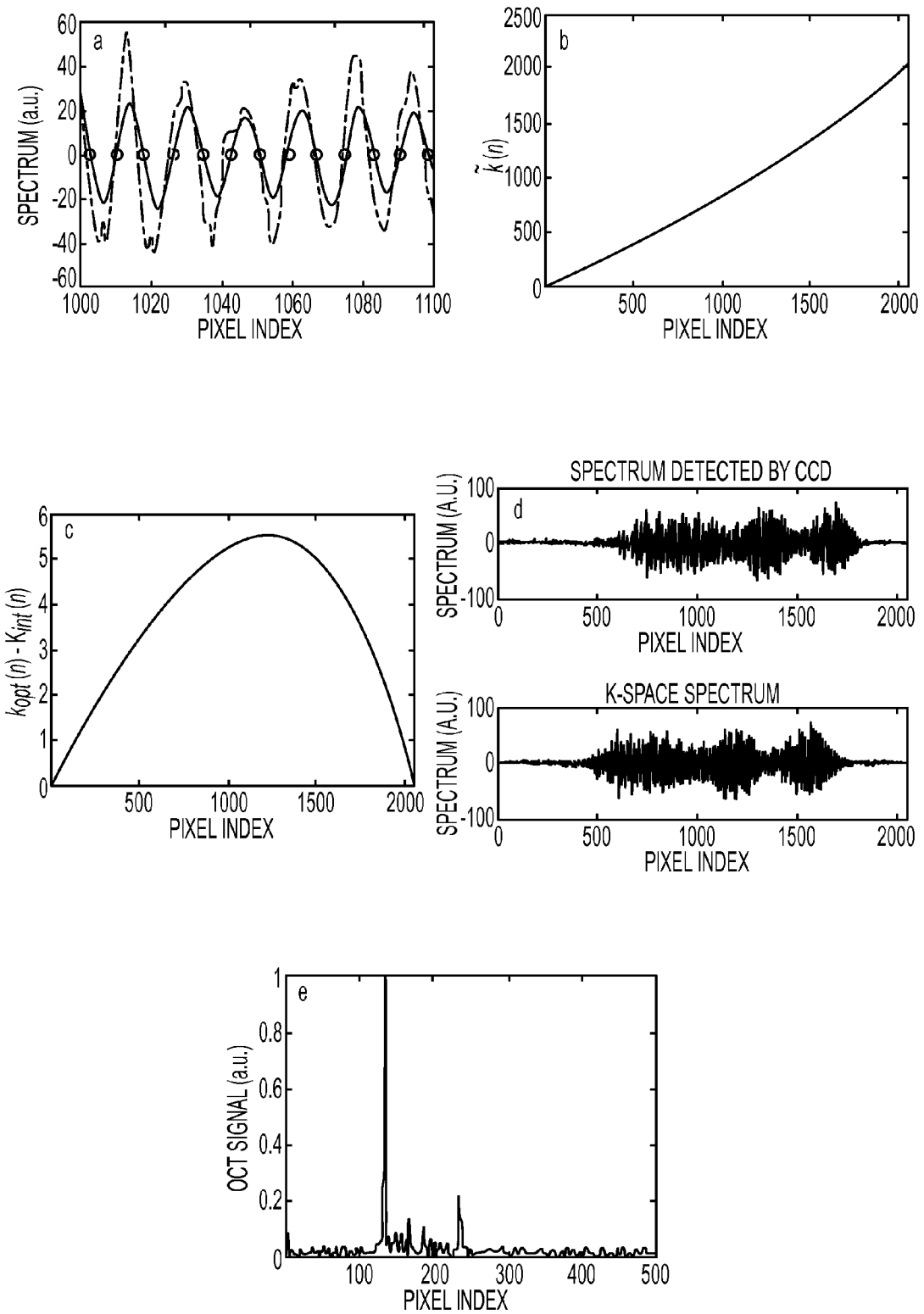
FIG. 3a shows interferometric fringes detected at the center part of a CCD (dash, original spectrum; solid, spectrum after bandpass filtering; circles, zero-crossing points)
FIG. 3b initial wavenumber mapping.
FIG. 3c difference between the initial estimation of wavenumber mapping and the wavenumber mapping that maximizes A-scan sharpness.
FIG. 3d interferometric fringes obtained from multilayered phantom, in pixel space (upper inset) and k-space (lower inset)
FIG. 3e A-scan corresponding to the spectrum in FIG. 3d.

We used a multilayered phantom sample that consisted of 6 layers of cellophane tape to generate data for calibration in the current example according to an embodiment of the current invention. We changed the robot position vertically with respect to the surface of the phantom at 2 μm increments and recorded 250 interferograms at resulting imaging depths. In principle, any of the interferograms can be used for ASC. However, an interferogram that has a larger fringe period will result in reduced error in zero-crossing detection; an interferogram that has a smaller fringe period will generate more zero-crossing points for the polynomial curve fitting. The spectrum used for calibration balances this tradeoff. In obtaining plots in FIGS. 3a-3e, we used an interferogram obtained when the sample surface was about 120 µm away from the reference plane for the calibration. FIG. 3a shows a section of the spectrum used for calibration, in which the light and dark curves are the original spectrum and the spectrum after bandpass filtering; the circles indicate zero-crossing points.

FIG. 3b shows the initial estimation of $\tilde{k}(n)$ obtained by polynomial curve fitting. We offset the $\tilde{k}(n)$ values and applied a scaling factor so that $\tilde{k}(n)$ ranges from 0 to 2047. Using the initial estimation of $\tilde{k}(n)$, we converted all of the 250 spectra to k-space and performed IFFT to obtain A-scans. We iteratively corrected the coefficients $a_1$, $a_2$, $a_3$, and $a_4$ to maximize the mean value of the sharpness merit M of all the A-scans. In FIG. 3c we plotted the difference between the initial estimation of the polynomial function and the polynomial function that maximizes A-scan sharpness. Based on $\tilde{k}(n)$ shown in FIG. 3b and the adjustment shown in FIG. 3c, we can convert the spectrum from pixel space to k-space, as shown in FIG. 3d (upper inset, the spectrum in pixel space; lower inset, the spectrum that has been converted to k-space). Performing IFFT on the k-space spectral interferogram shown as the red curve in FIG. 3d, we are able to obtain the A-scan as shown in FIG. 3e, which indicates that the sample used to generate calibrating data has complex internal structures.

Figures 4A, 4B, 4C, 4D:
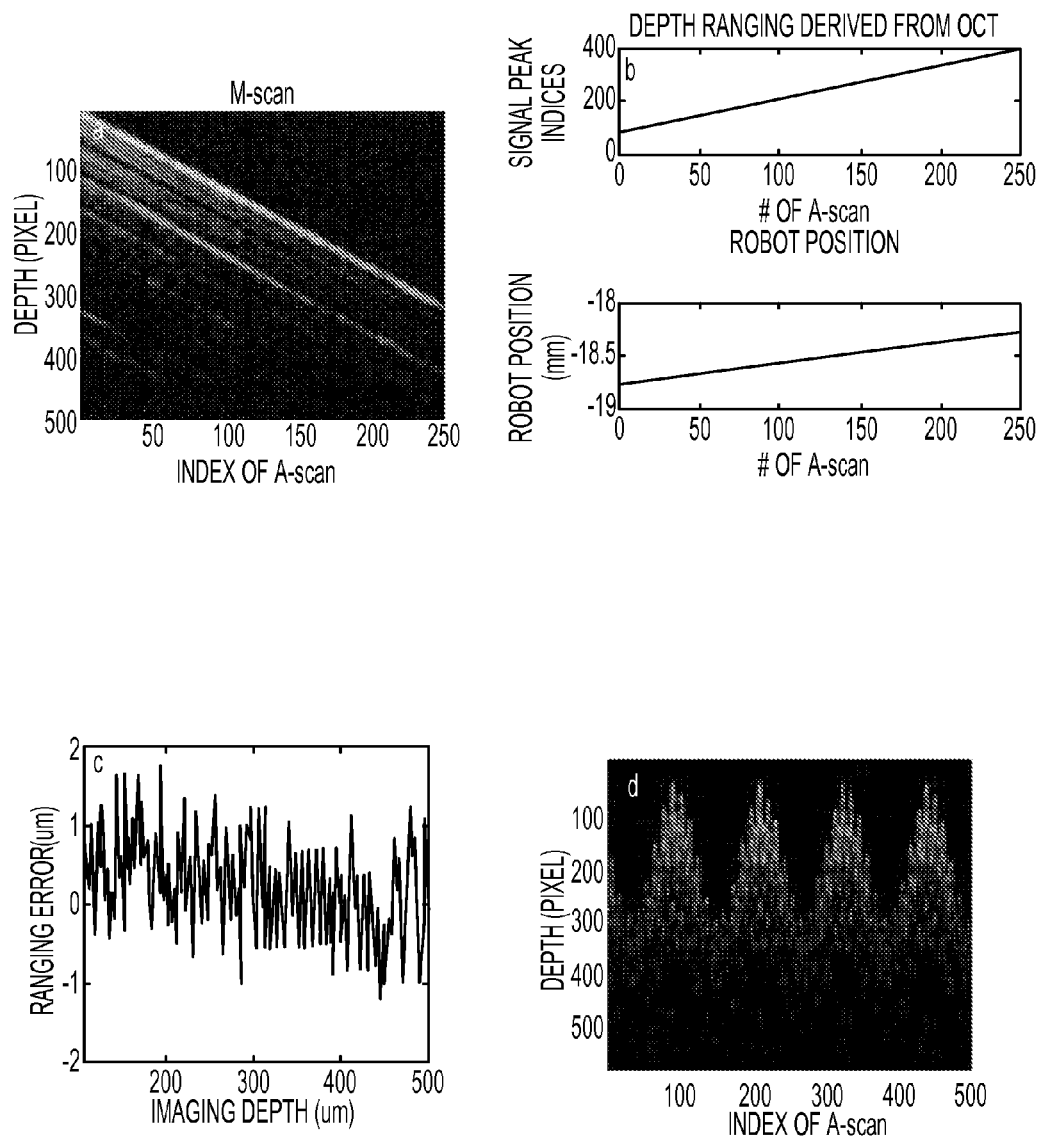
FIG. 4a shows an M-scan obtained when scanning the OCT probe axially above a multilayered phantom.
FIG. 4b robot motion derived from OCT signal in the unit of pixel (upper); commanded robot motion in mm (lower)
FIG. 4c ranging error based on regression using FIG. 4b.
FIG. 4d M-scan obtained when the OCT probe was modulated sinusoidally and the sample was nonstatic.

Based on the polynomial $\tilde{k}(n)$ obtained after the iterative algorithm, we convert all of the 250 spectra to k-space and obtain A-scans that have different peak indices, shown as M-scan in FIG. 4a. FIG. 4b shows the distance between reference plane and sample surface derived from the OCT signal (upper) and the command that drives the robot motion (lower). Assuming the sample is static, we obtain the pixel spacing Δz in A-scan to be 1.6 µm/pixel by solving the linear model shown in Eq. (5) by least squares regression. The R-square statistic of the regression is larger than 0.99, indicating the result is highly reliable. To test the ranging accuracy, we conducted another experiment. We imaged a mirror at different imaging depths and detected the index of the signal peak of A-scan and calculated the robot z-position $\tilde{z}$ with Equation (5). Applying offsets to $\tilde{z}$ and the commanded robot displacement Z so that they both start from 0, we compared $\tilde{z}$ with Z. The difference between $\tilde{z}$ and Z is shown is in FIG. 4c, which has a mean of 0.14 µm and a standard deviation of 0.61 µm. The small mean value indicates a high ranging accuracy over the imaging depth of interest. The 0.61 µm standard deviation falls within the system tolerance and the ranging error mainly come from the positioning error of the robot and the finite OCT pixel spacing.

Figures 4E, 4F, 4G:
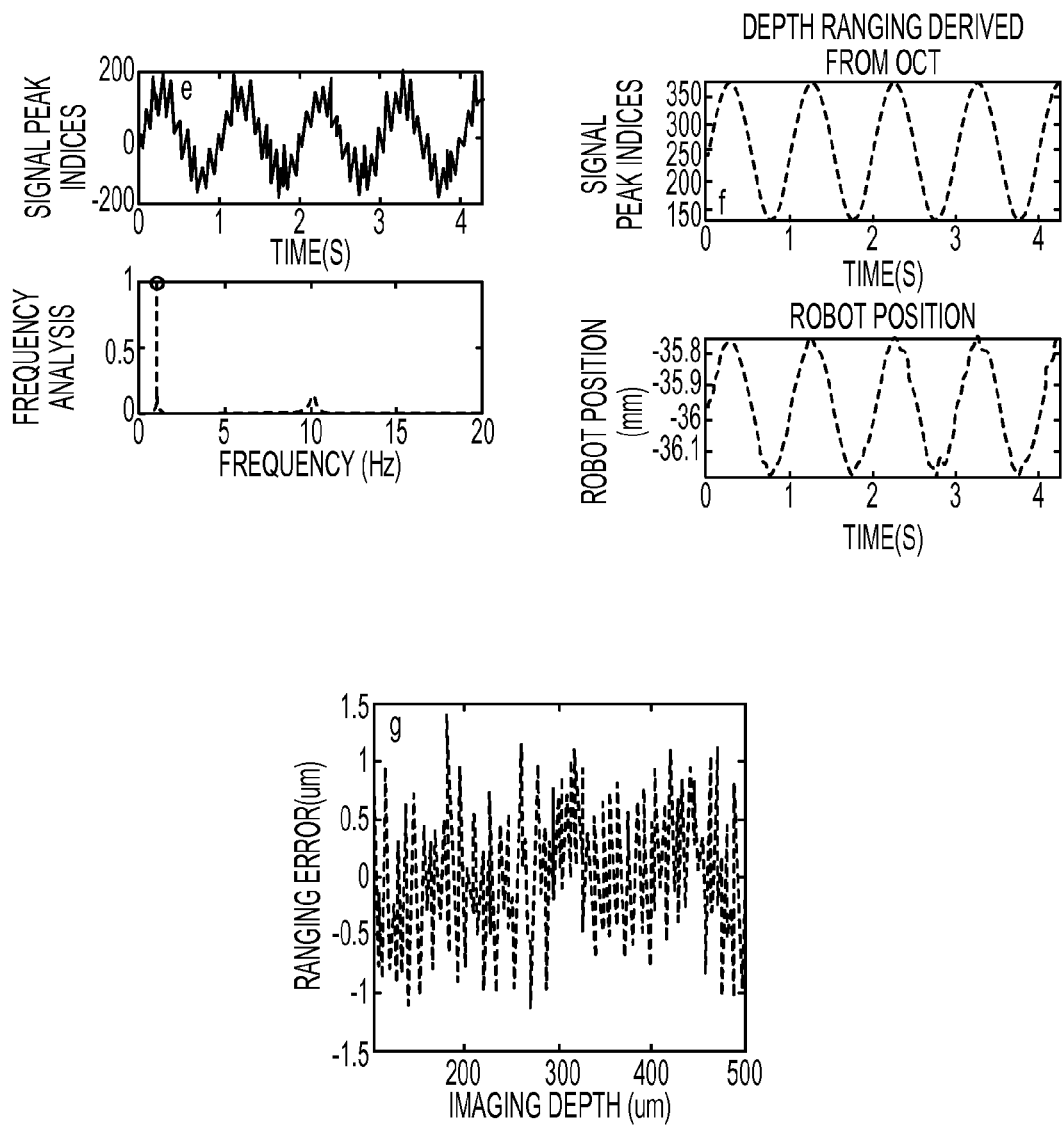
FIG. 4e OCT Signal peak indices (upper) and its frequency analysis result (lower)
FIG. 4f robot motion derived from OCT signal in the unit of pixel (upper); commanded robot motion in mm (lower)
FIG. 4g ranging error based on regression of FIG. 4f.

In order to calibrate the pixel spacing with a nonstatic sample, we modulated the robot's Z position with a sinusoidal wave. The sample, a multilayered cellophane-tape phantom, was driven by an actuator to move in-line with the robot's Z axis. Using one of the interferograms to generate a calibrating polynomial, we obtained an M-scan as shown in FIG. 4d, which shows the robot's vertical motion which was modulated with 1 Hz, 400 µm peak-to-peak sinusoidal wave and the sample was driven by a 10 Hz sinusoidal wave. For each A-scan, we detect the peak index. The peak indices in the A-scans, corresponding to the surface of our phantom, are plotted in FIG. 4e. The lower plot in FIG. 4e shows the result of frequency analysis of the signal peak position. Two frequency peaks appear at 1 Hz and 10 Hz, corresponding to the motion of the robot and the sample, respectively. Using a bandpass filter, we were able to separate the known robot motion at 1 Hz from the sample motion. FIG. 4f shows the robot position in pixel derived from OCT signals after bandpass filtering (upper) and commanded robot position in mm (lower). Using results shown in FIG. 4f and performing regression as shown in Equation (7), we calculated the pixel spacing to be 1.6 µm/pixel, which is identical to our previous result. FIG. 4g shows the difference between robot z-position (distance to sample surface) measured with the OCT and commanded position.

Figure 5A:
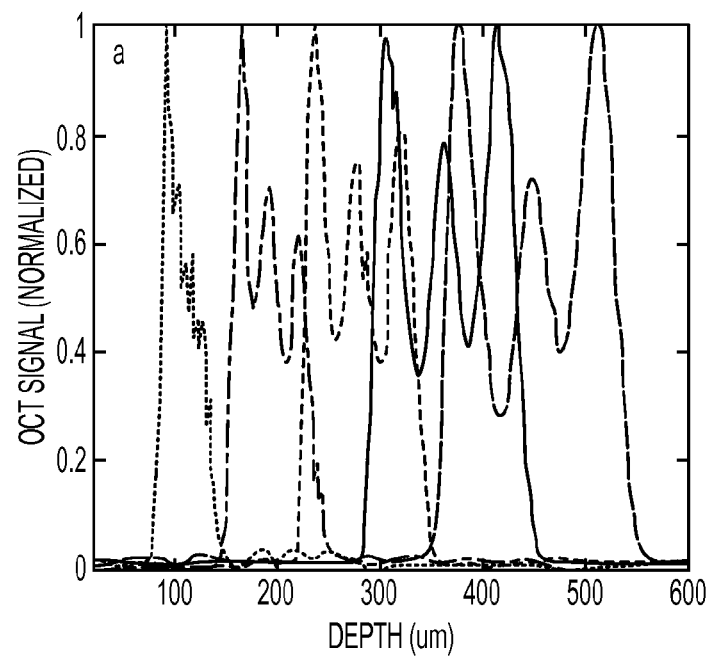
FIG. 5a shows PSFs obtained without calibration.
Figure 5B:
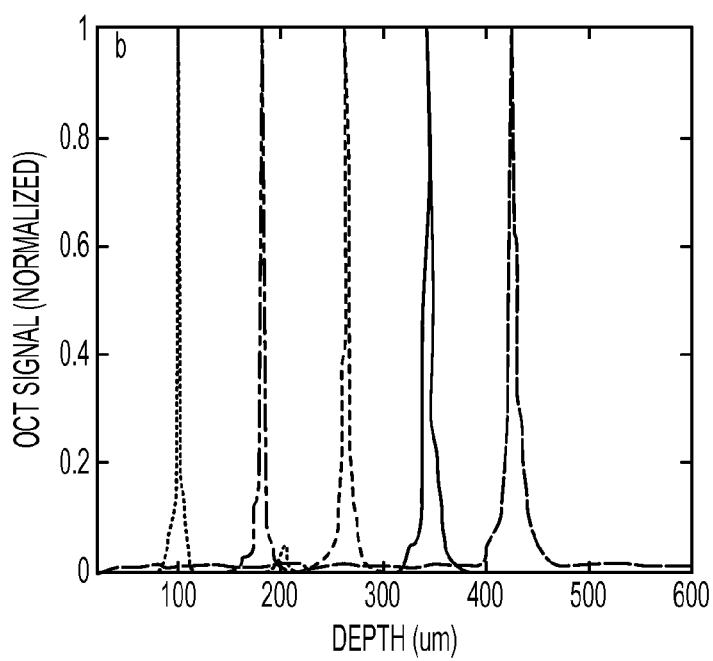
FIG. 5b PSFs obtained with calibration based on the initial estimation of the fourth order polynomial.
Figure 5C:
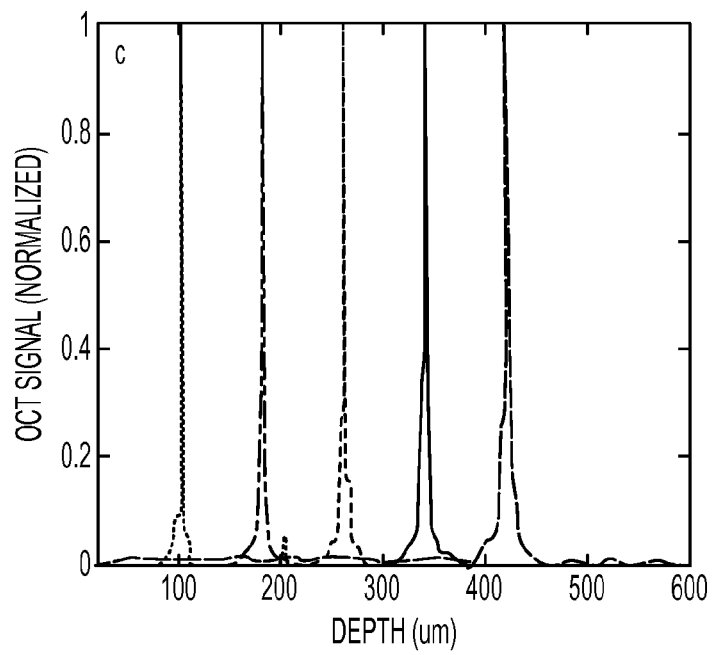
FIG. 5c PSFs obtained with calibration based on the fourth order polynomial that maximizes the image sharpness.
Figure 5D:
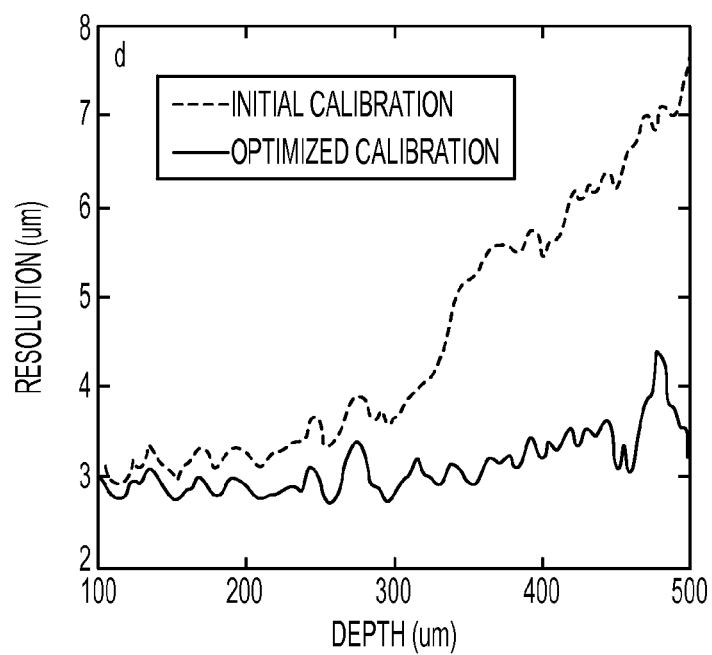
FIG. 5d FWHM resolution at different depths based on initial estimation of polynomial (blue) and the polynomial that maximizes the signal sharpness (red).

To evaluate the performance of the ASC method, we measured the axial PSF of our system by imaging a mirror at different depths. FIGS. 5a, 5b, and 5c show PSFs obtained without converting the spectral data to k-space, PSFs obtained from k-space spectral data using the initial estimation of the fourth order polynomial, and PSFs obtained from k-space spectral data using fourth order polynomial that maximizes the image sharpness. FIG. 5a shows the extremely broadened PSFs. PSFs in FIGS. 5b and 5c are much narrower compared to the ones in FIG. 5a. While PSFs in FIG. 5b show slight broadening as the imaging depth increases, PSFs in FIG. 5c stay almost constant over the entire imaging depth. The difference can be more clearly seen in FIG. 5d, which shows the axial resolution defined as the FWHM of the PSF at various imaging depths. When the optical path length difference between the reference and sample is small, both calibrations lead to about 3.2 µm resolution. With a larger distance between the reference and sample, the calibration based on the initial estimation of polynomial leads to a poorer resolution.

Figure 6A:
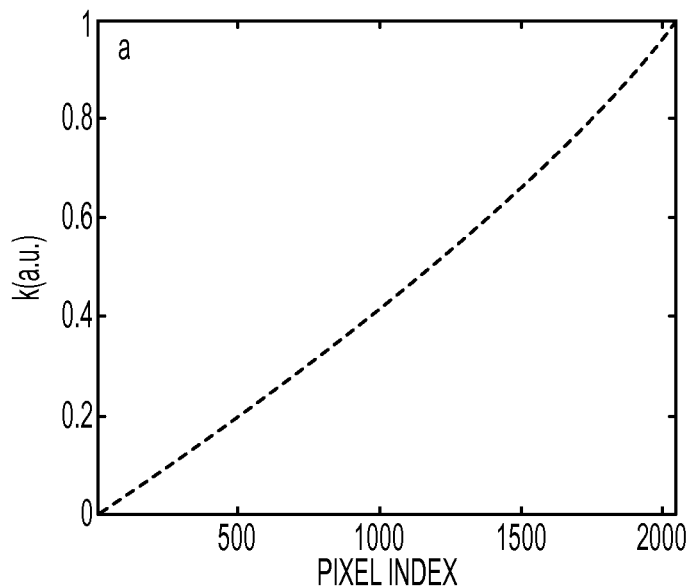
FIG. 6a provides ground truth wavenumber versus pixel index according to an embodiment of the current invention.
Figure 6B:
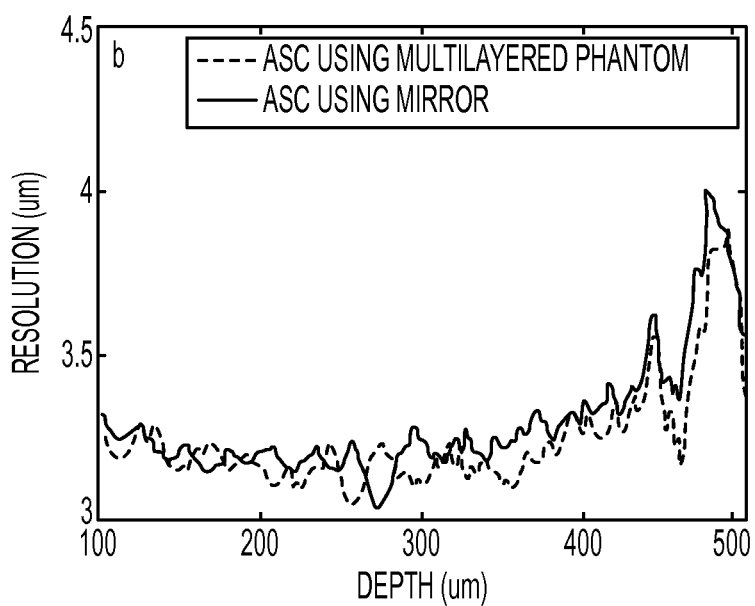
FIG. 6b provides FWHM resolution at different depths using interferograms from a multilayered phantom by ASC (dot) and from a mirror by extracting the phase (solid).

To demonstrate that calibrating data generated from a multilayered phantom can lead to comparable performance as calibrating data with a perfect sinusoidal modulation, we used our CP FD-OCT to image a mirror and calibrated our spectrometer by extracting the phase of the interferogram using a similar method as one proposed by M. Mujat et al. The obtained k(n) is resealed to [0 1] and shown in FIG. 6a, which will be used as a ground truth to compare with result of our ASC method in this example. We evaluated the performance of calibration using axial resolution defined as FWHM of the PSF. Based on the calibrating polynomials obtained, we measured the axial resolution corresponding to ASC calibration, as well as ground truth calibration, $\delta z_{ASC}$ and $\delta z_{groundtruth}$ at different imaging depths (see FIG. 6b). Although the interferograms captured from a multilayered phantom and mirror are significantly different, FIG. 6b shows that the performance of ASC using a multilayered phantom and the ground truth calibration using a mirror are similar. We calculated the difference between $\delta z_{Asc}$ and $\delta Z_{groundtruth}$; the difference between them turned out to have a mean value of 0.1129 µm, indicating that our ASC using a sample with complex internal structure has satisfactory performance compared to conventional spectral calibration methods.

Figure 7A:
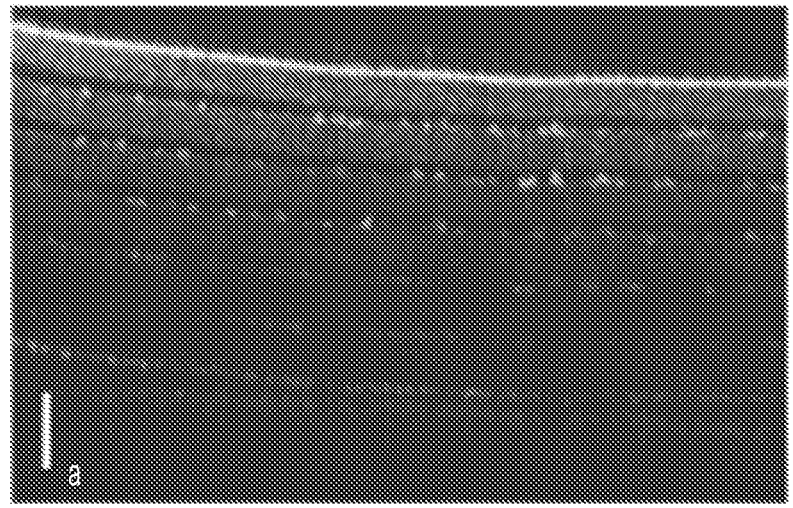
FIGS. 7a and 7b show images of a multilayer phantom obtained with (a) and without (b) ASC.
Figure 7B:
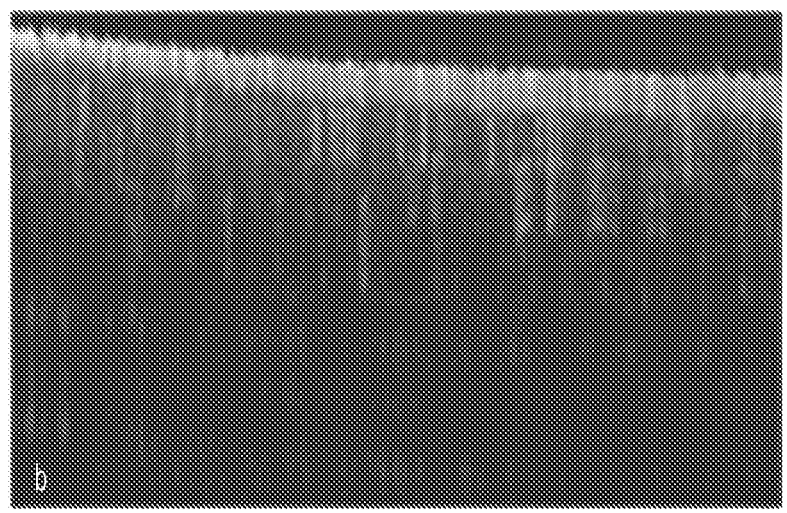

We scanned the fiber probe laterally over the multilayered phantom and obtained a B-mode OCT image based on the result of ASC according to an embodiment of the current invention. The result is shown in FIG. 7a (the scale bar indicates 100 µm). In FIG. 7a, tape layers are clearly visible. As a comparison, FIG. 7b shows the OCT image obtained by directly performing IFFT on the spectral data detected by the CCD. The layer structure is hardly discernable in FIG. 7b.

Figure 8A:
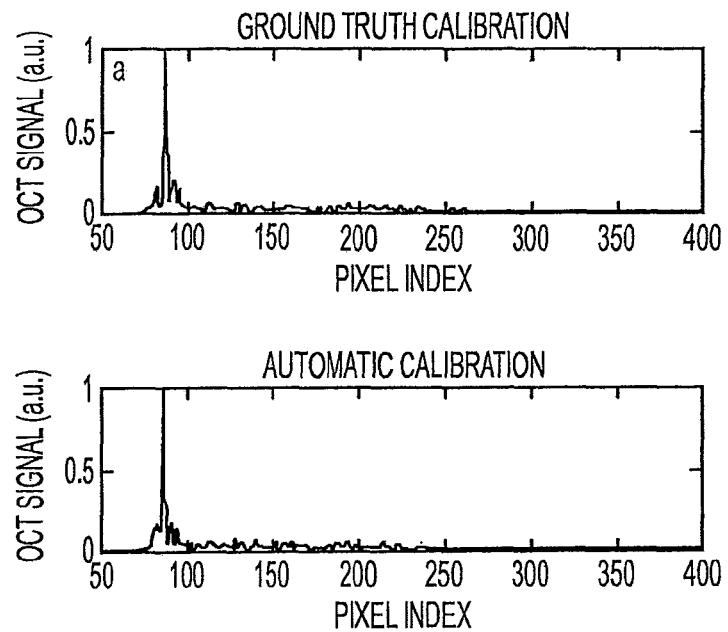
FIG. 8a shows A-scans based on ground truth calibration (upper inset) and automatic calibration (lower inset) according to an embodiment of the current invention.
Figure 8B:
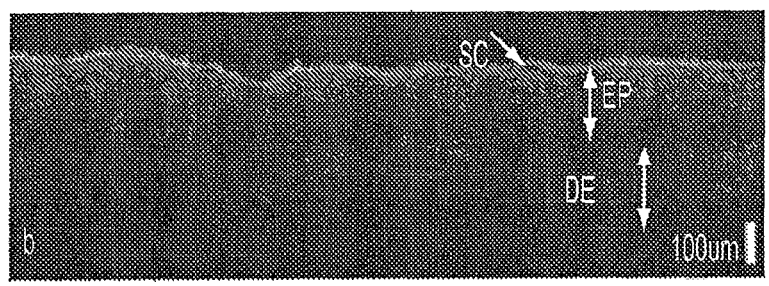
FIG. 8b M-scan OCT image of human forearm skin, based on ground truth calibration (SC: stratum corneum; epidermis: EP; dermis: DE)
Figure 8C:
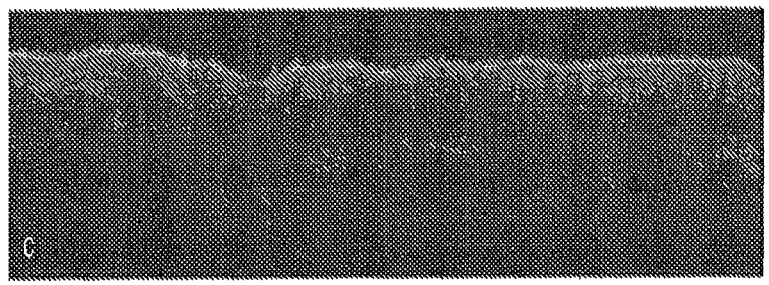
FIG. 8c M-scan OCT image of human forearm skin, based on automatic calibration according to an embodiment of the current invention.

To verify that our CP FD-OCT generates sufficient signals for zero-crossing detection in the automatic calibration algorithm from human tissue, we used the CP FD-OCT probe that is a single mode fiber integrated with metal tube to manually scan the skin at the forearm of a healthy human volunteer. We chose one of the spectra for automatic spectral calibration. Again, we use the ground truth calibration shown in FIG. 6a for comparison. The particular spectrum is subsequently converted to k-space according to the "ground truth" calibration result, and according to the result based on our ASC algorithm which uses the same spectrum to generate spectral mapping. The A-scans obtained are shown in FIG. 8a as curves in upper and lower insets. It is clear that the sample surface generates a large signal peak in the A-scan; moreover, A-scans overlap well. We processed all of the obtained spectra using both calibrations (ground truth and automatic calibration). However, one problem involved in freehand scanning is the image artifact due to variations in the scan velocity. As a result of the changing scan velocity, some areas of an image may be undersampled and others are oversampled. To correct for such artifacts, we used a novel technique based on the cross-correlation of A-scans within a 2-D OCT image to assemble M-scan OCT images (A. Ahmad, S. G. Adie, E. J. Chaney, U. Sharma, and S. A. Boppart, "Cross-correlation-based image acquisition technique for manually-scanned optical coherence tomography," Opt. Express 17, 8125-8136 (2009)). The 2D images obtained are shown in FIGS. 8b and 8c, which are on ground truth calibration and the ASC methods according to some embodiments of the current invention. In both images, stratum corneum (SC), epidermis (EP) and dermis (DE) tissue are visible. We obtained identical images using ground truth and ASC methods, which verifies the effectiveness the effectiveness of our method for in vivo data according to some embodiments of the current invention.

While conventional OCT systems are typically calibrated in a lab setting, our method can be used "on-the-fly" which allows monitoring of OCT system performance during a scanning operation or between scans. This is possible because the spectral data for our ASC method can be a conventionally scanned image, i.e., spectral interferogram captured from a sample with complex internal structures. This can be a compelling feature for safety reasons as well as convenience—especially for portable systems that might be used in surgical settings or any mission critical applications.

Furthermore, when using the OCT data for image-guided interventions or general metrology, pixel size calibration is necessary. According to an embodiment of the current invention, we achieved the A-scan pixel size calibration by modulating the motion of the robot holding the probe to encode its position relative to the moving sample. This relative motion is extracted from the OCT data and compared with the commanded robot motion. A simple regression procedure can be used to extract the A-scan pixel size. The motion profile can be any function that is significantly different from the assumed sample motion. For robustness, we can use multiple, superimposed periodic profiles, e.g., 10 hz+3 hz. Methods according to some embodiments of the current invention assume that the sample motion is not affected by the motion of the probe. This might not be true if the displaced fluid in front of the oscillating probe compresses or translates the sample tissue, especially if the probe has a profile with large surface area and is close to the sample surface. Although examples provided used a sophisticated surgical robot, the A-Scan pixel spacing calibration can apply to systems integrated with an axial actuator and can be performed with a static or moving sample.

Due to the random nature of the scanning environment and complex sample structure, it is possible for a "bad" interferogram to be captured that may not to lead to a high quality calibration. However, multiple A-scans are often acquired and, thus, provide multiple samples from which one can choose to provide an optimized calibration result.

If an OCT system suffers from both dispersion mismatch and non-equally k-space sampling, calibration according to some embodiments of the current invention can compensate for nonlinear phase originated from both. Therefore, the result is not merely a k-space calibration according to some embodiments of the current invention. To use ASC methods in OCT systems based on Michelson interferometers with a significant amount of dispersion mismatch for spectrometer calibration according to some embodiments of the current invention, one can incorporate a common path interferometer into a conventional Michelson interferometer by blocking the reference arm and inserting a partial reflector in front of the sample. For a fiber-optic based system, this can be achieved by using a single mode fiber with cleaved tip at the sample arm of the Michelson interferometer; for an OCT system based on bulky optics, a common-path interferometer can be configured by adding a thin glass cover slide at the end of the sample arm.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A method for calibrating a Fourier domain optical coherence tomography system, comprising:
    receiving spectral data from an optical detector comprising a linear array of detector elements, each detector element having a position labeled n, wherein detected light was wavelength-dispersed across said linear array of detector elements;
    determining parameters of a preselected functional relationship between wave number, $k_n$, corresponding to detector element n as a function of optical detector element n based on said spectral data;
    further receiving subsequent spectral data subsequent to the first-mentioned receiving, wherein detected light was wavelength-dispersed across said linear array of detector elements;
    converting said subsequent spectral data using said preselected functional relationship between wave number $k_n$ and optical detector element n to obtain converted spectral data; and
    performing an inverse Fourier transform of said converted spectral data to obtain a depth profile.

2. The method of claim 1, wherein said preselected functional relationship is a polynomial.

3. The method of claim 2, wherein said preselected functional relationship is $$k_n = a_4 n^4 + a_3 n^3 + a_2 n^2 + a_1 n + a_0,$$

wherein said determining parameters is determining parameters $a_0$, $a_1$, $a_2$, $a_3$, and $a_4$.

4. The method of claim 1, wherein said determining parameters includes a zero crossing analysis of said spectral data.

5. The method of claim 1, wherein said determining parameters includes an iterative process taking into account a sharpness of an interferogram based on said spectral data.

6. The method of claim 1, further comprising calibrating a depth corresponding to each detector element of said linear array of detector elements.

7. The method of claim 6, wherein said calibrating a depth comprises moving a reference of said Fourier domain optical coherence tomography system along a predefined path.

8. The method of claim 7, wherein said predefined path is a substantially periodic path.

9. The method of claim 7, wherein said predefined path is a substantially sinusoidal path.

10. A non-transitory computer readable medium comprising software, which software when executed by a computer causes the computer to:
receive spectral data from an optical detector comprising a linear array of detector elements, each detector element having a position labeled n, wherein detected light was wavelength-dispersed across said linear array of detector elements;
determine parameters of a preselected functional relationship between wave number, $k_n$, corresponding to detector element n as a function of optical detector element n based on said spectral data;
further receive subsequent spectral data subsequent to the first-mentioned receiving, wherein detected light was wavelength-dispersed across said linear array of detector elements;
convert said subsequent spectral data using said preselected functional relationship between wave number $k_n$ and optical detector element n to obtain converted spectral data; and
perform an inverse Fourier transform of said converted spectral data to obtain a depth profile.

11. The computer readable medium of claim 10, wherein said preselected functional relationship is a polynomial.

12. The computer readable medium of claim 11, wherein said preselected functional relationship is $$k_n = a_4 n^4 + a_3 n^3 + a_2 n^2 + a_1 n + a_0,$$

wherein said determining parameters is determining parameters $a_0$, $a_1$, $a_2$, $a_3$, and $a_4$.

13. The computer readable medium of claim 10, wherein said determining parameters includes a zero crossing analysis of said spectral data.

14. The computer readable medium of claim 10, wherein said determining parameters includes an iterative process taking into account a sharpness of an interferogram based on said spectral data.

15. The computer readable medium of claim 10, wherein said software when executed by said computer further causes the computer to calibrate a depth corresponding to each detector element of said linear array of detector elements.

16. The computer readable medium of claim 15, wherein said calibrating a depth comprises moving a reference of said Fourier domain optical coherence tomography system along a predefined path.

17. The computer readable medium of claim 16, wherein said predefined path is a substantially periodic path.

18. The computer readable medium of claim 16, wherein said predefined path is a substantially sinusoidal path.

19. An automatic spectral calibration optical coherence system, comprising:
a reference;
an optical probe;
a light source optically coupled to said optical probe;
a spectrometer detection system optically coupled to said optical probe; and
a computer constructed to communicate with said spectrometer detection system while in operation,
wherein said computer is configured to:
receive spectral data from an optical detector comprising a linear array of detector elements, each detector element having a position labeled n, wherein detected light was wavelength-dispersed across said linear array of detector elements;
determine parameters of a preselected functional relationship between wave number, $k_n$, corresponding to detector element n as a function of optical detector element n based on said spectral data;
further receive subsequent spectral data subsequent to the first-mentioned receiving, wherein detected light was wavelength-dispersed across said linear array of detector elements;
convert said subsequent spectral data using said preselected functional relationship between wave number $k_n$ and optical detector element n to obtain converted spectral data; and
perform an inverse Fourier transform of said converted spectral data to obtain a depth profile.

20. The automatic spectral calibration optical coherence system of claim 19, wherein said preselected functional relationship is a polynomial.

21. The automatic spectral calibration optical coherence system of claim 20, wherein said preselected functional relationship is $$k_n = a_4 n^4 + a_3 n^3 + a_2 n^2 + a_1 n + a_0,$$

wherein said determining parameters is determining parameters $a_0$, $a_1$, $a_2$, $a_3$, and $a_4$.

22. The automatic spectral calibration optical coherence system of claim 19, wherein said determining parameters includes a zero crossing analysis of said spectral data.

23. The automatic spectral calibration optical coherence system of claim 19, wherein said determining parameters includes an iterative process taking into account a sharpness of an interferogram based on said spectral data.

24. The automatic spectral calibration optical coherence system of claim 19, wherein said software when executed by said computer further causes the computer to calibrate a depth corresponding to each detector element of said linear array of detector elements.

25. The automatic spectral calibration optical coherence system of claim 24, wherein said calibrating a depth comprises moving a distal end of an optical probe of said Fourier domain optical coherence tomography system along a predefined path.

26. The automatic spectral calibration optical coherence system of claim 25, wherein said predefined path is a substantially periodic path.

27. The automatic spectral calibration optical coherence system of claim 25, wherein said predefined path is a substantially sinusoidal path.

* * * * *